United States Patent
Silver et al.

(10) Patent No.: US 9,517,294 B2
(45) Date of Patent: Dec. 13, 2016

(54) PROCESS FOR USE WITH BREASTPUMP TO INITIATE MILK IN BREASTFEEDING, PARTICULARLY FOR PREMATURE INFANTS

(71) Applicant: Medela Holding AG, Baar (CH)

(72) Inventors: Brian H. Silver, Cary, IL (US); Paula Meier, Oak Park, IL (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 14/727,840

(22) Filed: Jun. 1, 2015

(65) Prior Publication Data

US 2016/0082164 A1 Mar. 24, 2016

Related U.S. Application Data

(63) Continuation of application No. 12/701,749, filed on Feb. 8, 2010, now Pat. No. 9,050,404.

(60) Provisional application No. 61/154,252, filed on Feb. 20, 2009.

(51) Int. Cl.
   *A61M 1/06* (2006.01)
   *A61M 1/00* (2006.01)

(52) U.S. Cl.
   CPC ........... *A61M 1/062* (2014.02); *A61M 1/06* (2013.01); *A61M 1/0031* (2013.01); *A61M 1/0037* (2013.01); *A61M 2205/50* (2013.01); *A61M 2205/52* (2013.01)

(58) Field of Classification Search
   CPC ..... A61M 1/0031; A61M 1/0037; A61M 1/06
   See application file for complete search history.

(56) References Cited

U.S. PATENT DOCUMENTS

| | | | |
|---|---|---|---|
| 4,573,969 A | 3/1986 | Schlensog et al. | |
| 5,571,084 A * | 11/1996 | Palmer | A61M 1/06 601/14 |
| 6,547,756 B1 | 4/2003 | Greter et al. | |
| 6,808,517 B2 | 10/2004 | Greter et al. | |
| 6,840,918 B1 * | 1/2005 | Britto | A61M 1/06 604/364 |
| 7,201,735 B2 * | 4/2007 | Atkin | A61M 1/06 604/74 |
| 9,050,404 B2 * | 6/2015 | Silver | A61M 1/06 |
| 9,162,016 B2 * | 10/2015 | Geddes | A61M 1/06 |
| 2003/0069536 A1 | 4/2003 | Greter et al. | |
| 2004/0215138 A1 | 10/2004 | Greter et al. | |

(Continued)

FOREIGN PATENT DOCUMENTS

| WO | WO 00/57934 A1 | 10/2000 |
|---|---|---|
| WO | WO 01/47577 A2 | 12/2001 |
| WO | WO 2009/081313 A1 | 7/2009 |

OTHER PUBLICATIONS

PCT International Search Report dated Jul. 6, 2010 for PCT/US2010/024572.

*Primary Examiner* — Aarti B Berdichevsky
(74) *Attorney, Agent, or Firm* — McDonnell Boehnen Hulbert & Berghoff LLP

(57) ABSTRACT

The present invention provides a suction sequence which is considered to produce advantageous results, particularly for mothers with newborn infants. The sequence comprises a process of stimulation, expression, and pausing to closely mimic a newborn's sucking pattern.

8 Claims, 7 Drawing Sheets

(56) References Cited

U.S. PATENT DOCUMENTS

| | | | |
|---|---|---|---|
| 2005/0234370 A1* | 10/2005 | Beal | A61H 9/0078 601/15 |
| 2007/0219486 A1 | 9/2007 | Myers et al. | |
| 2008/0097290 A1 | 4/2008 | Geddes | |
| 2008/0177224 A1* | 7/2008 | Kelly | A61M 1/0037 604/74 |
| 2011/0004154 A1 | 1/2011 | Van Schijndel et al. | |

* cited by examiner

PROCESS FOR USE WITH BREASTPUMP TO INITIATE MILK IN BREASTFEEDING, PARTICULARLY FOR PREMATURE INFANTS

CROSS-CITE TO RELATED APPLICATIONS

This application is a continuation application of U.S. patent application Ser. No. 12/701,749 filed Feb. 8, 2010, which claims priority to U.S. Provisional Application Ser. No. 61/154,252, filed on Feb. 20, 2009, both of which are incorporated herein by reference in their entirety.

FIELD OF THE INVENTION

This invention relates generally to a method for expressing breastmilk, and most particularly to a process for initiating breastmilk from a mother very shortly after giving birth, most particularly in the instance of a premature infant, using a motorized, such as electrically driven, breastpump.

BACKGROUND

Breastpumps for use by nursing mothers are well known. They allow the nursing woman to express the breastmilk as necessary or convenient, and further provide collection of the breastmilk for later use. For some mothers, breastpumps may be a necessity, such as when the child has suckling problems, or if the mother has problems with excessive or deficient milk production, or soreness, deformation, or injury of the mammilla. Of particular instance herein is the situation confronting a mother where the infant is premature, and therefore is most always separated from the mother.

Electrically-driven breastpumps are commonplace, typically including a vacuum pump which has an electric motor that plugs into standard house current, and/or operates off of battery power. Advantages of this type of pump are convenience, ready controllability and regulation of the vacuum, and in many instances the ability to pump both breasts at once.

Electrically driven motorized breastpumps generally have a driving mechanism for generating the vacuum (negative pressure) to be applied at the breast geared to a particular sequence, or curve, of negative pressure increase (i.e., increasing suction), and then release. This is often aimed at reproducing in some sense the suckling action of a healthy infant during mature lactation, after the milk supply has been established.

Mothers with healthy full-term infants can usually breastfeed during the early days after birth. In the early days after birth, the maternal milk supply is limited, and includes colostrum. Colostrum ingestion in the very earliest stages of post-partum life is considered to be highly valuable to the newborn infant. Newborns have very small stomachs, and they remove only about 15 mL of colostrum during the first 24 hours of life. Colostrum is known to contain antibodies that are major components of the immune system, anti-inflammatory agents and growth factors that stimulate the development of the gut. During the early post-partum period when the mother is producing colostrum, the human newborn infant sucks in a unique sucking pattern, which is characterized by a rapid rate of sucking, and an irregular sucking rhythm (organization of sucking into bursts and pauses). After lactogenesis II (the milk "coming in") this sucking pattern changes because human infants modify the sucking rhythm on the basis of available milk. The slower rate and regular rhythm of sucking after lactogenesis II result from the infants' integrating swallowing and breathing into the sucking bursts. Thus, the sucking pattern used during the first days post-birth (prior to lactogenesis II) is time-limited and unique to human breastfeeding infants. Several lines of evidence suggest that this sucking pattern plays a role in subsequent maternal milk output.

A mother may not be able to breastfeed within the first few days after birth. Additionally, not all infants are born full-term. Preterm or premature babies are often defined as babies born before 37 weeks gestation; however a "premature" infant may also be defined as one that has not yet reached the level of fetal development that generally allows life outside the womb. In the United States, the preterm birth rate has risen to 12-13% in recent decades. When a baby is born premature, the baby is often in the Neonatal Intensive Care Unit (NICU) and may not be able to breastfeed. Thus, the mother is solely breast-pump dependent. Breast-pump dependent mothers do not experience this unique sucking pattern from their premature infants who are not capable of feeding directly from the breast. Because this unique sucking pattern appears to be a critical "first step" in establishing an adequate milk volume, breast pump-dependent mothers with premature infants may miss this critical stimulation, negatively affecting their ability to produce a sufficient amount of milk.

SUMMARY OF THE INVENTION

The present invention is an improved method for initiating the expression of milk for an infant. In its preferred form, it is a method adapted for use with a motor-driven pump, such as an electric or battery operated breastpump. More particularly, the present invention has a principal objective of providing a method especially useful to express milk in the early days after birth of an infant, and most particularly in the instance of a premature infant. It will be understood that while the invention is generally discussed in the particular environment of being present on a program for a computer-driven breastpump for a mother of a premature infant, other situations and devices for carrying out the process are contemplated and will fall within the scope of the invention.

The method in one embodiment provides a breast pump suction pattern designed to be closer to that of the breastfeeding human infant prior to the onset of lactogenesis II. This pattern is important for a mother who has given birth to a premature infant, or to an infant who must remain in the NICU and is not available to feed initially at the breast, thus providing the mother with the unique stimulatory sucking pattern.

Put another way, an aspect of the invention is to substantially recreate the unique sucking pattern used by the human newborn prior to the onset of lactogenesis II. This is of particularly significant application when dealing with the mother of a premature infant, because the infant cannot provide the necessary stimulation to the mother's breast. With this inventive method, the mother will be now be able to use a suction pattern in the breastpump to initiate her lactation as if the infant were not premature. Additionally, use of this pattern increases maternal milk output during the first 14 days post-birth, and thus is considered to improve the volume of the supply of milk overall (post-initiation).

Another aspect of the invention is the incorporation into a preset pattern a set of suction sequences which are non-repeating, or do not appear to be repeating to the mother, in order to mimic the irregular sucking rhythm used by healthy term infants prior to the onset of lactogenesis II. In a preferred embodiment, one or more stimulation sequences are arranged into a pattern lasting approximately 10-20 minutes. This pattern (or set of sequences) is broken up by pauses of an extended duration at seemingly random times in the pattern. Another preferred embodiment includes expression sequences, where at least one stimulation sequence and one expression sequence are arranged into a pattern lasting approximately 10-20 minutes. The stimulation sequences and expression sequences are arranged in a manner such that the sequences occur at, seemingly to the mother, unpredictable times in the pattern, providing the mother a seemingly random order having seemingly random sequence durations broken up by pauses of an extended duration, generally greater than about 5 seconds.

In an exemplary embodiment, the pattern comprises either a stimulation sequence, an expression sequence, or a combination thereof, followed by an extended pause, then another combination of one or more stimulation sequences and/or expression sequences ensues. In this exemplary embodiment, another extended pause may follow, and at the end of the pause another stimulation sequence follows, or an expression sequence, or a combination thereof.

In one preferred embodiment, the pattern comprises the steps of stimulating at a higher cycle rate (of about 120 cycles per minute) with a moderate vacuum for a plurality of minutes, preferably about three minutes; then exerting a pull and release cycle at about the same vacuum, but at a somewhat lower (slower) rate (of about 90 cycles per minute) for about two minutes; then expressing at a higher vacuum but slower more standard rate (of about 30-60 cycles per minute) for about one minute; pausing (for about ten seconds); then exerting another pull and release cycle for about one minute; then stimulating again for a plurality of minutes, preferably about two minutes; pausing for about ten seconds; then stimulating once again for about two minutes; exerting another pull and release cycle for about a minute; then another expressing cycle for about one minute; pausing for about ten seconds; and then once more exerting a pull and release cycle for about one and a half minutes.

In another embodiment, the pattern preferably comprises the steps of exerting a pull and release cycle at about 120 cycles per minute at a vacuum level of about between 70 and 200 mmHg for approximately three minutes; exerting a pull and release cycle at about 90 cycles per minute at a vacuum level of about between 70 and 200 mmHg for approximately two minutes; expressing at about between 34 and 54 cycles per minute at a vacuum level of about between 100 and 250 mmHg for approximately one minute; pausing for approximately ten seconds; exerting a pull and release cycle at about 90 cycles per minute at a vacuum level of about between 70 and 200 mmHg for approximately one minute; exerting a pull and release cycle at about 120 cycles per minute at a vacuum level of about between 70 and 200 mmHg for approximately two minutes; pausing for approximately ten seconds; exerting a pull and release cycle at about 120 cycles per minute at a vacuum level of about between 70 and 200 mmHg for approximately two minutes; exerting a pull and release cycle at about 90 cycles per minute at a vacuum level of about between 70 and 200 mmHg for approximately one minute; expressing at about between 34 and 54 cycles per minute at a vacuum level of about between 100 and 250 mmHg for one minute; pausing for approximately ten seconds; and exerting a pull and release cycle at about 90 cycles per minute at a vacuum level of about between 70 and 200 mmHg for approximately one and a half minutes.

As will be discussed further herein, variations in these patterns of sequences are contemplated.

These and other advantages of the invention will be further understood upon consideration of the following detailed description of certain embodiments, taken in conjunction with the drawings, in which:

DETAILED DESCRIPTION

Figure 1:
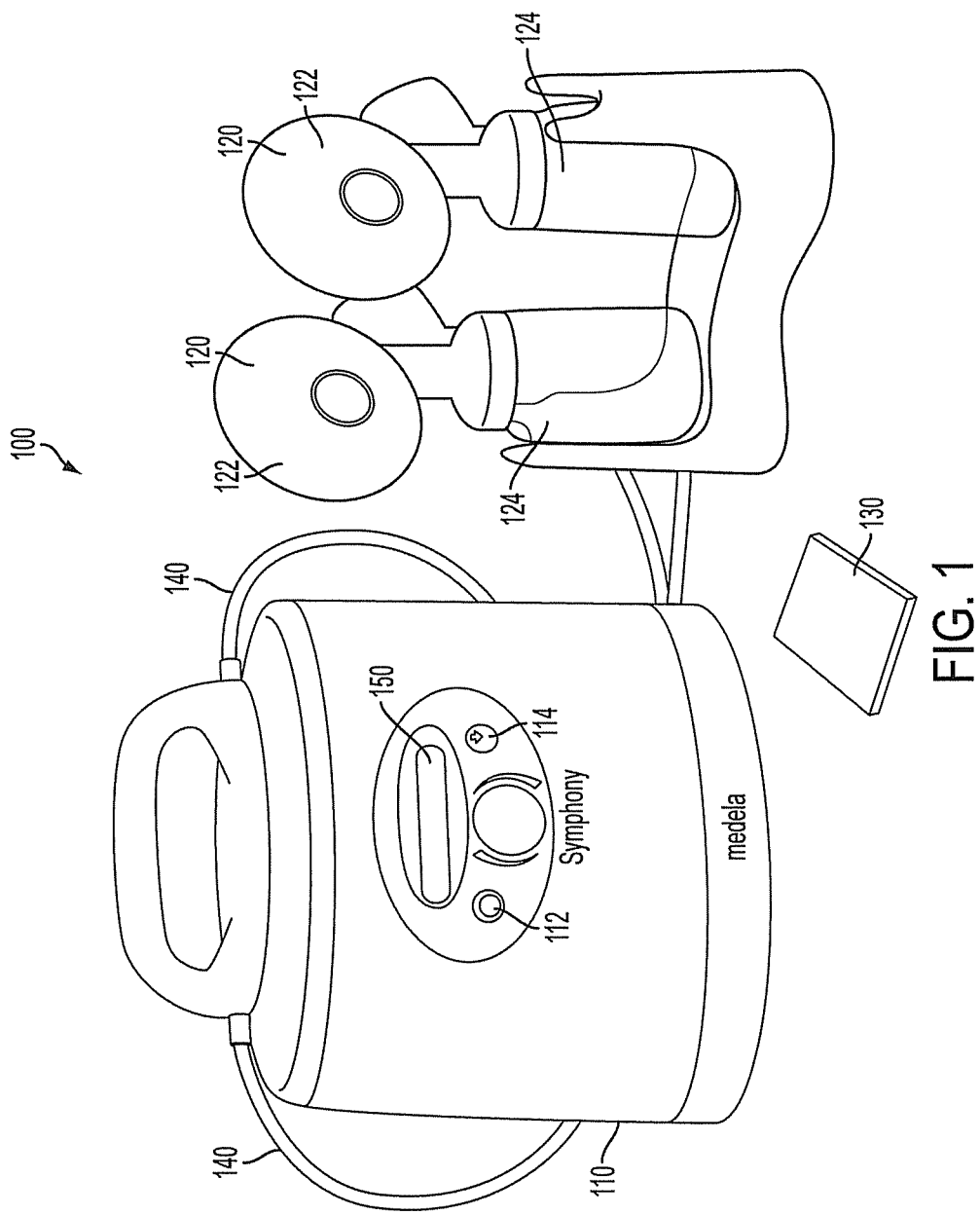
FIG. 1 is an illustration of a breastpump assembly for use in accordance with one embodiment of the present invention.

FIG. 1 is an illustration of a breastpump assembly in accordance with one embodiment of the present invention. This is the SYMPHONY breastpump made and sold by Medela, Inc. That breastpump is generally described in U.S. Pat. No. 6,547,756, the contents of which are fully incorporated herein, and reference thereto can be made for salient details of this breastpump. While the invention has found particular application for use with this kind of programmable breastpump and with respect to premature babies, it can be used or adapted for use with other motorized pumps capable of being operated with the varying sequences (hereinafter described), and aspects are considered adaptable to full-term babies.

As shown in FIG. 1, breastpump assembly 100 includes a breastpump apparatus 110, a plurality of breastshield and container assemblies 120, and a program card 130. Power may be provided to breastpump apparatus 110 either through standard current via a power cord, a battery, or some other appropriate power supply.

One significant aspect of the present invention is the ability to operate, as by program, the breastpump with different types of suction sequences in a selected order. The breastpump 110 utilizes a microprocessor-based system which is provided user input through a program card, such as program card 130. Breastpump apparatus 110 has a program card insert slot through which a user inserts program card 130. Once inserted, program card 130 is read. The particular program on the program card 130 is then communicated to the microprocessor. The microprocessor is integrated with a drive unit to effect operation of the drive unit in accordance with the selected program. Again, details of pump operation can be gleaned from the aforementioned U.S. Pat. No. 6,547,756, or the SYMPHONY machine itself. Use of this programmable breastpump 110 is considered ideal, in that the program card embodiment is extremely user-friendly. It will be understood that the invention could be effected in some other manner, as by a pump dedicated to just this program of sequences, or a drive mechanism/controller which is capable of triggering the sequences in a desired order.

One embodiment contemplated, for instance, provides a sequence that can be engaged without need of a separate program card for the same. In this embodiment, the sequence is pre-programmed in the microprocessor, or may otherwise be wired into the circuitry in a manner to override the then-existing operating program. When the mother desires to engage this sequence, she presses a particular button, which activates the program.

Returning now to FIG. 1, breastpump apparatus 110 may be either a double or a single pump. The single pump extracts milk from one breast at a time, and the double pump can be used to extract milk from both breasts at the same time. Breastpump apparatus 110 is attached to each of the plurality of breastshield and container assemblies 120 with a tube 140. Each of the plurality of breastshield and container assemblies 120 comprises a breastshield 122 and a container 124. Container 124 is used to store the pumped milk.

To extract breastmilk from a mother, breastshields 122 are placed and centered over a mother's nipples. Breastpump apparatus 110 may be turned on by a user pressing a first button 112, and in this embodiment, program card 130 is used with the apparatus. The apparatus reads the program contained on program card 130. Breastpump apparatus 110 may display instructions to the user via interface 150. The instructions may ask the user to start the program. If the mother wants to start the program, the mother may press a second button 114. Interface 150 may then show instructions and/or graphics that let the mother know that the program is starting.

The program card 130 may operate a preset pattern comprised of non-repeating suction sequences. Alternatively, the program card 130 may operate a preset pattern comprised of repeating suction sequences that appear to be non-repeating to the user, due to the overall length of the pumping session such that the sequences seem to be occurring at unpredictable times in the pattern with extended pauses between some of the sequences. An extended pause is a pause that is approximately greater than about five seconds in duration. Some of the pauses may be of shorter duration, however, but still of a length that yields a noticeable hiatus to the mother.

The sequences comprise at least one stimulation sequence and one expression sequence, and may additionally comprise at least one pull and release cycle. These are most preferably mixed in the program.

Figure 2:
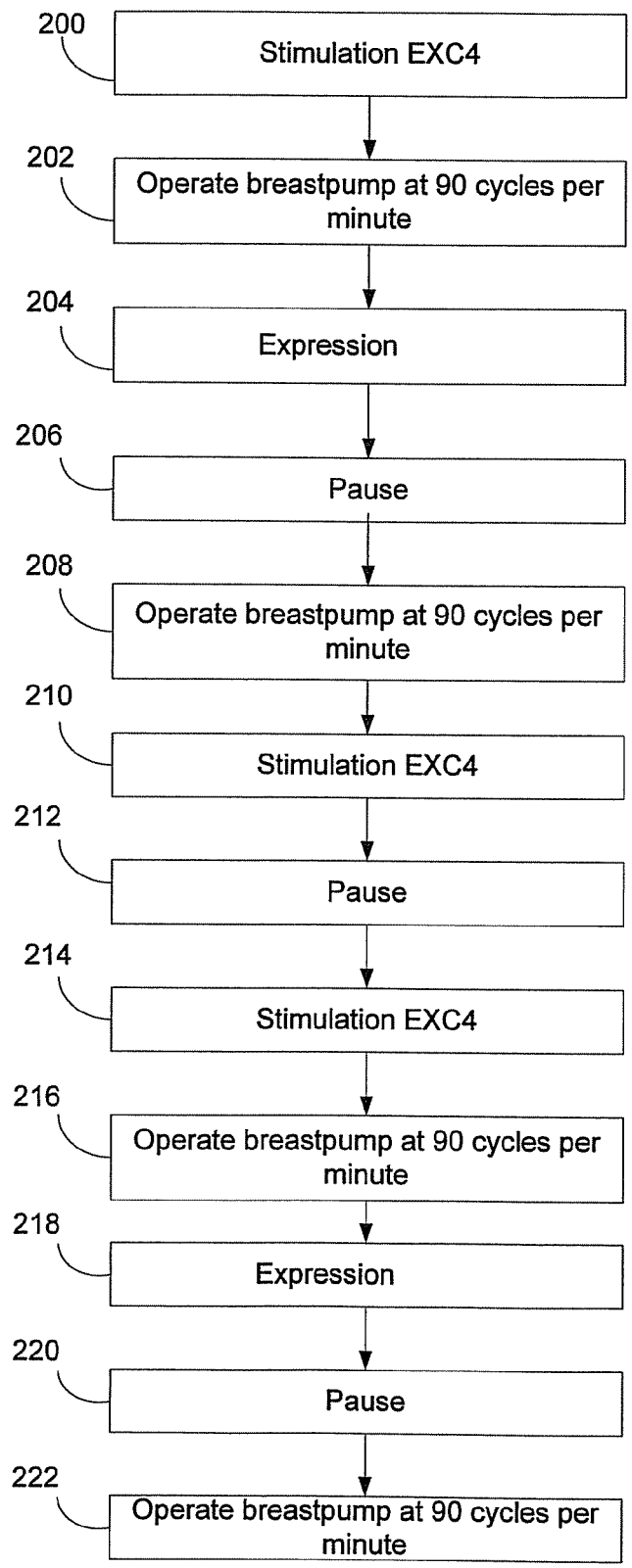
FIG. 2 is a simplified chart of a process to initiate milk flow from a mother's breast in accordance with exemplary embodiments of the invention.
Figure 3:
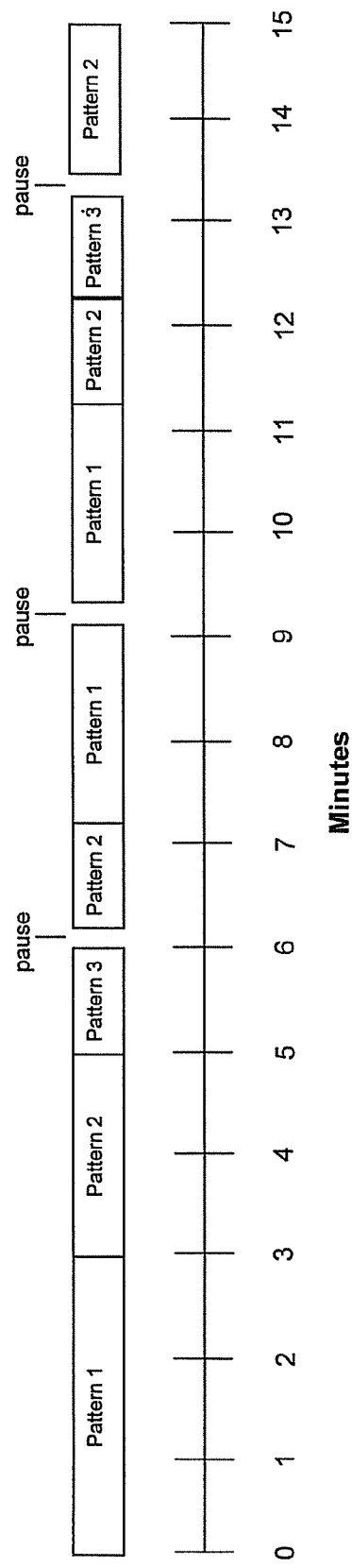
FIG. 3 is a diagram of a process to initiate milk flow from a mother's breast in accordance with exemplary embodiments of the invention.

FIGS. 2 and 3 depict examples of how the program card 130 may operate to initiate flow from a mother's breast in accordance with one aspect of the present invention. The process on program card 130 is identified here as the "Preemie+ 1.0" program. The steps in FIGS. 2 and 3 are designed so that a most-desired pattern of stimulation, expression, and pauses is provided. This particular set of sequences and pauses is considered to more closely resemble the sucking pattern of a newly-born infant during the early days post-birth before the onset of lactogenesis II. See, e.g., JAN RIORDAN & KATHLEEN AUERBACH, BREASTFEEDING AND HUMAN LACTATION 94 et seq. (2d ed. 1999), regarding stages of lactation and lactogenesis in particular. At birth, prolactin levels remain high, while the delivery of the placenta results in a sudden drop in progesterone, estrogen, and HPL levels. The abrupt withdrawal of progesterone in the presence of high prolactin levels stimulates the copious milk production of lactogenesis II. When the breast is stimulated, prolactin levels in the blood rise, triggering the cells in the alveoli to make milk. The sequences described in FIGS. 2 and 3 are designed to stimulate the breast and eventually achieve the lactogenesis II stage. It will be understood, however, that while the particular set of sequences and pauses set forth in the presently most-preferred embodiment have achieved significant results and advantages, the set may well be reducible, yet still achieve some or all of the desired purposes. Substantially recreating the suckling pattern of a newborn baby pre-lactogenesis II is most desired, and some other mix of various stimulation cycles and pauses may serve the desired end. Precision in the patterns used, their order, and the number of pauses and duration of the same is not considered critical. It is the fact that the overall combination for the first time in a breastpumping method has the capability of reproducing the sucking pattern of the very early newborn, pre-lactogenesis II.

In FIG. 2, at step 200, stimulation sequence C4 "(EXC4)" is set into motion for approximately three minutes. Stimulation EXC4 has a moderate vacuum level at a higher cycle rate of about 120 cycles per minute.

At step 202, the breastpump is now operated at another stimulation sequence of about 90 cycles per minute (cpm) for approximately two minutes. The cycles per minute indicate the sucking rhythm, or the number of pulls and releases per minute. The "sucking" comprises a vacuum (negative pressure).

At step 204, an expression sequence is set into motion for approximately one minute. This expression sequence has a relatively higher vacuum level operated at a slower cycle rate.

At step 206, the breastpump is paused for ten seconds. During the pause step, a zero or near zero negative pressure (ambient) remains relatively constant.

At step 208, the breastpump is operated at the lower stimulation sequence of 90 cpm for approximately one minute.

At step 210, stimulation pattern EXC4 is again set into motion for approximately two minutes.

At step 212, the breastpump is paused for ten seconds.

At step 214, stimulation expression sequence EXC4 is repeated for approximately two minutes.

At step 216, the breastpump is operated at the slower stimulation sequence of 90 cpm for approximately one minute.

At step 218, the expression sequence is once more set into motion for approximately one minute.

At step 220, the breastpump is paused for ten seconds.

At step 222, the breastpump is operated at the slower stimulation sequence of 90 cpm for approximately one and a half minutes.

Steps 200 through 222 are designed to last for approximately fifteen minutes total, which is considered to resemble the sucking duration of a term infant and also aids in acceptability among pump-dependent mothers with premature infants. After fifteen minutes, the program may shut off automatically. At the present time, pauses on the order of greater than or equal to five seconds are considered to be sufficient and preferred, with ten seconds plainly yielding desirable results.

The mother may use the method described in steps 200-222 frequently. As an example, the mother may use the method 8-10 times daily. The method may be used in combination with a "standard" pattern, such as the Standard 2.0 program made and sold by Medela, Inc. That pattern is also generally described and shown in U.S. Pat. No. 6,547, 756, and reproduced here at FIG. 7. Both the pattern described by the method in steps 200-222 and the Standard 2.0 program may be combined onto one program card 130.

FIG. 3 shows a diagram of a process to initiate milk flow from a mother's breast in accordance with an exemplary embodiment. In FIG. 3, pattern 1 comprises operating the breastpump at about 120 cpm with a vacuum level in the range of about 70-200 millimeters of mercury, or torr (mmHg). Pattern 2 comprises operating the breastpump at 90 cpm with a vacuum level in the range of about 70-200 mmHg. Pattern 3 comprises operating the breastpump between about 34 and 54 cpm, with a vacuum level in the range of about 100-250 mmHg.

Pattern 1 is operated for approximately three minutes, pattern 2 is then operated for 2 minutes, and pattern 3 is then operated for approximately one minute. A pause then ensues for ten seconds. During the pause, pressure remains constant. Pattern 2 is operated for approximately one minute, followed by pattern 1 for approximately two minutes. A pause ensues for ten more seconds. Pattern 1 is operated for approximately two minutes, followed by pattern 2 for approximately one minute, and then pattern 3 for approximately one minute. A pause ensues for ten more seconds. Pattern 2 is then operated for approximately one and a half minutes.

Example 1

A study was conducted to evaluate the effectiveness of different pumping patterns that could assist mothers of premature infants in initiation. One-hundred and five mothers enrolled in the study within 24 hours after birth. Since the level of prematurity may have affected the mammary development, the mothers were assigned randomly to generate an appropriate distribution of infants born at less than 27 weeks gestation, and infants born at more than 27 weeks gestation.

The mothers were divided into three groups. Group I used the initiation pattern present on the Preemie+ 1.0 program until the onset of lactogenesis II, and then switched to an experimental maintenance pattern. Group II used the initiation pattern present on the Preemie+ 1.0 program until the onset of lactogenesis II and then switched to the pattern present on program card 130 called the Standard 2.0 card. Group III used the Standard 2.0 program to both initiate until the onset of lactogenesis II and to maintain lactation.

Figure 4:
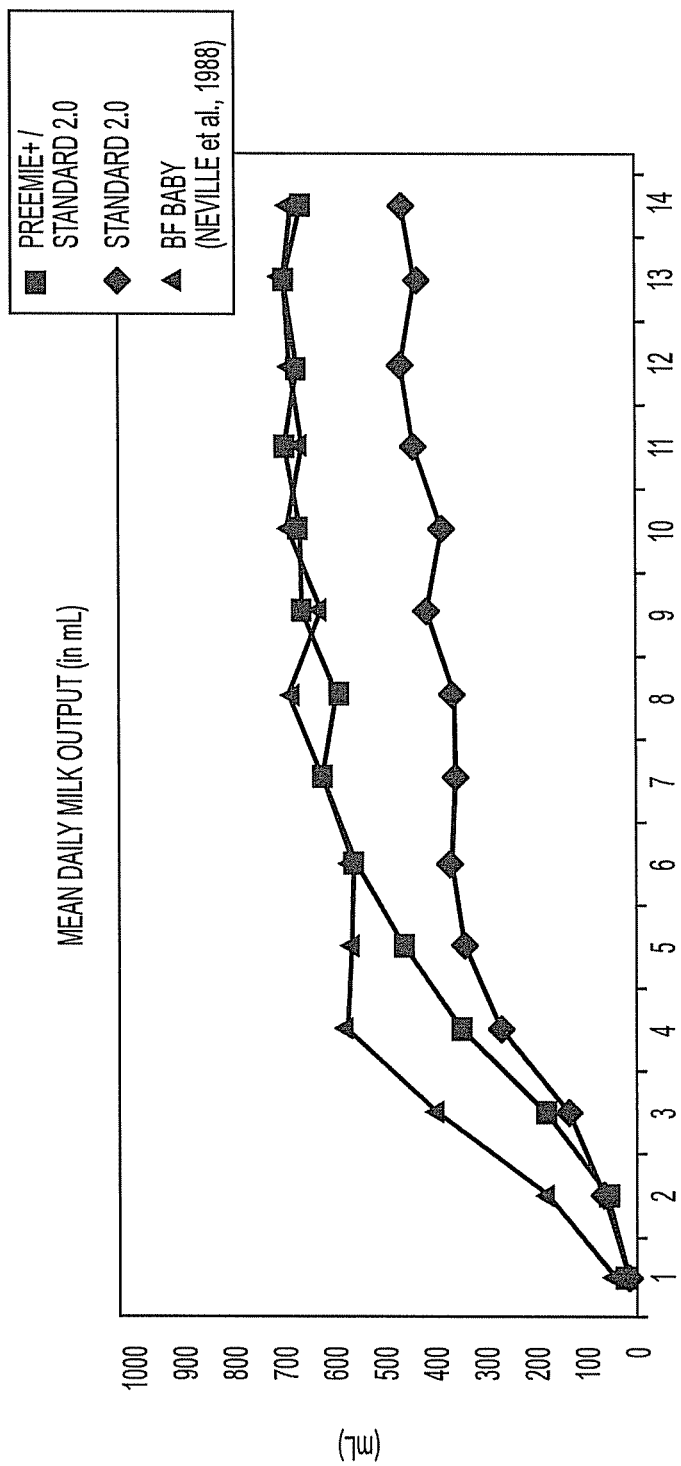
FIG. 4 is a graph that shows the mean daily milk output from a mother's breast over the first fourteen days after birth of the infant.

FIG. 4 is a graph that shows the mean daily milk output over the first fourteen days after birth of the infant (Groups II and III). The statistics for a breastfed baby ("BF Baby") were taken from the article Neville et al., from 1988. FIG. 4 shows that by day 6, mothers in Group II achieved as much milk as mothers of exclusively breastfeeding term infants.

Figure 5:
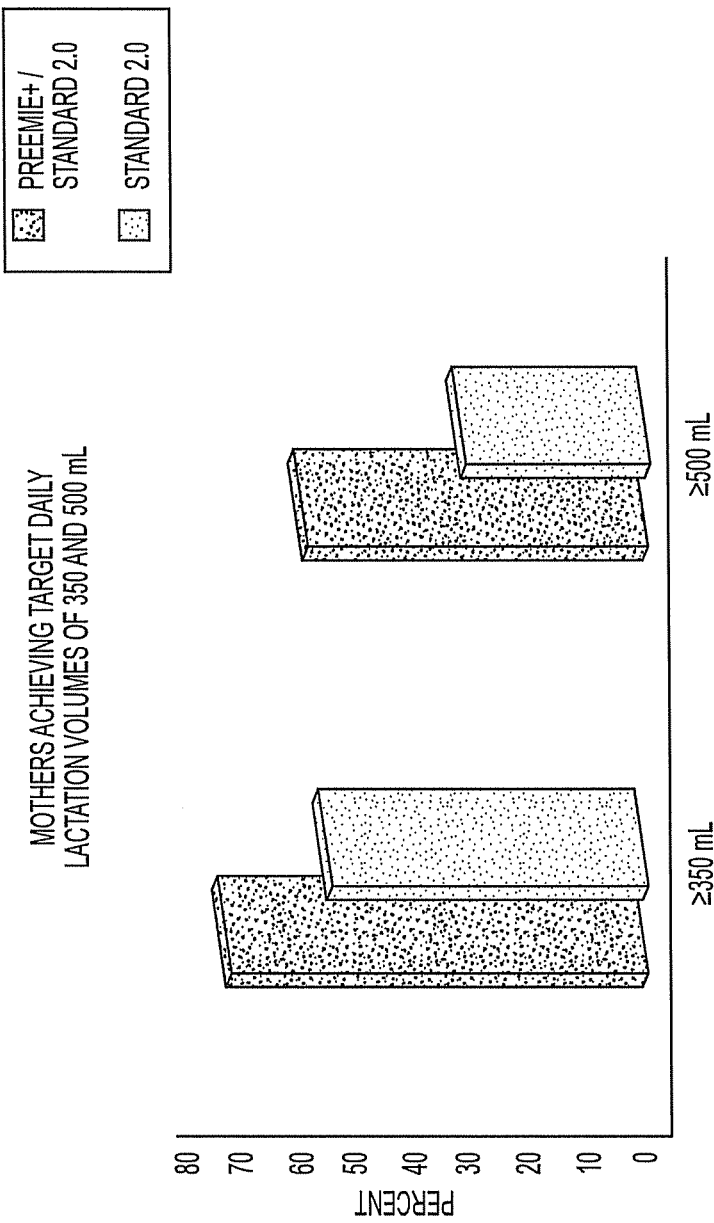
FIG. 5 is a bar chart that shows the percentage of mothers achieving the target daily lactation volumes of 350 and 500 mL using a process according to the invention.

FIG. 5 is a bar chart that shows the percentage of mothers achieving the target daily lactation volumes of 350 and 500 mL by day fourteen. By day fourteen, 36% more mothers from Group II than mothers from Group III achieved the milk output target of ≥350 mL/day, which is a sufficient amount to exclusively feed human milk to a premature infant at NICU discharge. More than twice the number of mothers from Group II achieved the milk output target of ≥500 mL/day than the mothers from Group III.

Figure 6:
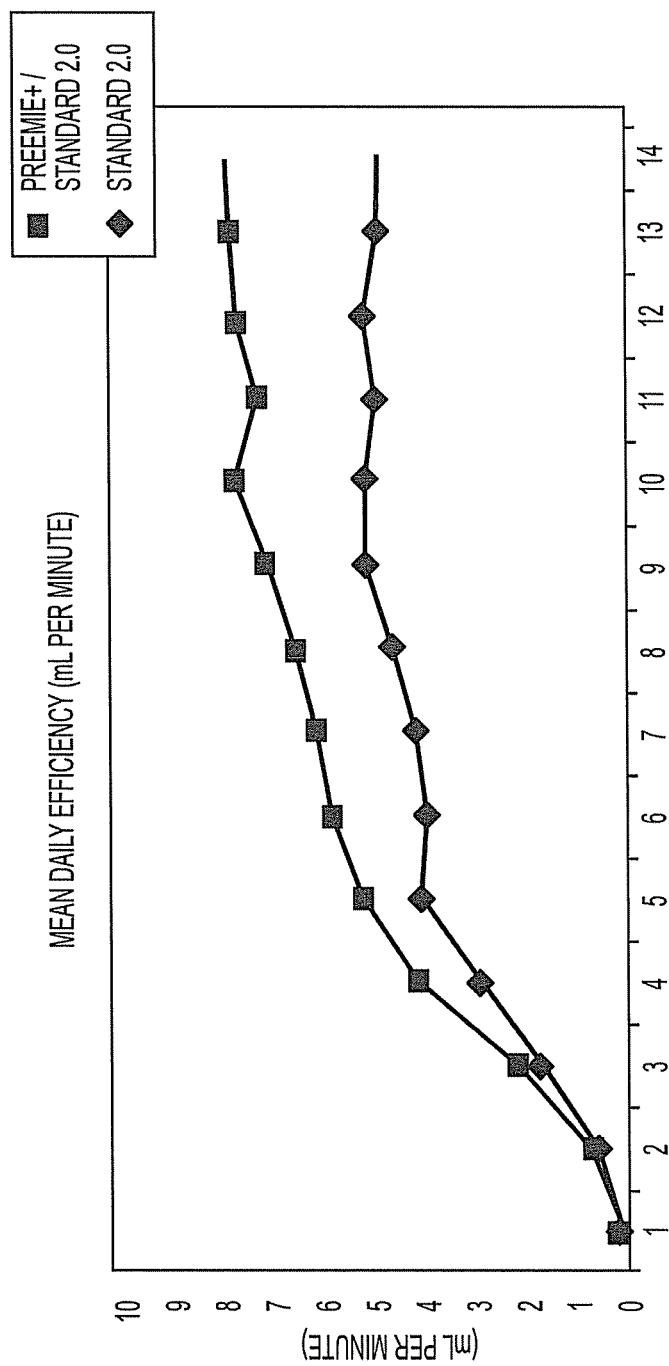
FIG. 6 is a graph that measures the mean daily efficiency of pumping over the first fourteen days after the birth of the infant using a process according to the invention.
Figure 7:
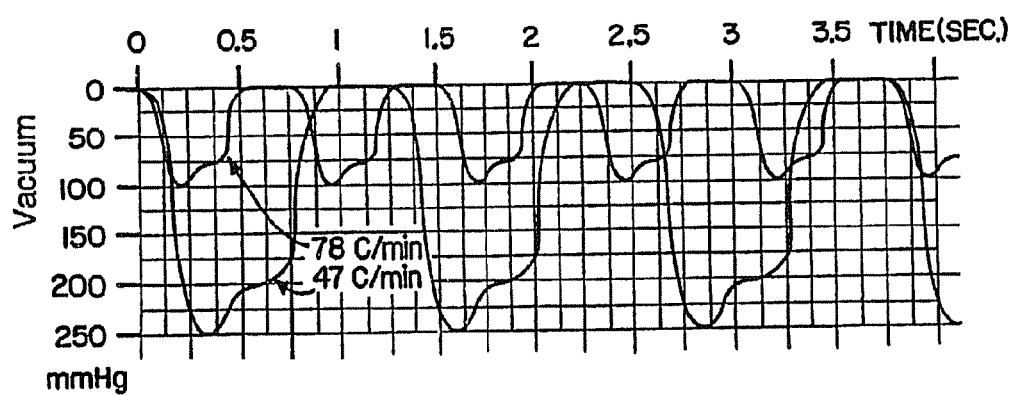
FIG. 7 is a graph of a so-called "standard" program sequence.

FIG. 6 is a graph that measures the mean daily efficiency of pumping, in milliliter per minute of milk flow, for each of the fourteen days. FIG. 6 compared the mean daily efficiency of the women in Group II to the women in Group III. The results were that on average, mothers from Group III pumped for 124 fewer minutes during the first 14 days. By day 4, pumping was approximately 50% more efficient. FIG. 7 is a graph of a so-called "standard" program sequence. The vacuum range is 100-250 mmHg and the cycles are 47-78 cycles/min automatically. This program also contains the milk let down program, with a vacuum range between 50-150 mmHg and cycles of 120-150 cycles/min. Eliminating even a few minutes of pumping and not have it compromise the mother's milk volume is a great advantage. The invention has yielded a method whereby mothers can achieve more milk volume in less time.

Various exemplary embodiments and methods have been described above. Those skilled in the art will understand, however, that changes and modifications may be made to those examples without departing from the scope and spirit of the present invention. For instance, the cycles indicated as well as the various negative pressures (vacuum levels) are to be given some latitude, and are not intended to be rigidly applied (e.g., "90 cpm" could be more or less, provided it yields the desired result in the overall grouping of sequences). And it should be noted that the above overview is meant to be illustrative, not limiting. That is, additional and/or different features may be present in some embodiments of the present invention.

What is claimed is:

1. A breastpump system comprising:
    a source of vacuum to cyclically deliver vacuum to a breastshield;
    at least one processor;
    memory storage;
    a first program stored on the memory storage which, when executed by the at least one processor causes the at least one processor to operate the source of vacuum, the first program comprising:
        providing a plurality of stimulation sequences for stimulating the breast using a rapid cycle rate;
        providing at least one expression sequence for extracting milk at a lower cycle rate; and
        operating the breastpump system according to at least one of a preset pattern of non-repeating sequences and a preset pattern of repeating sequences wherein certain of the repeating sequences occur in the pattern at unpredictable times to a user, the non-repeating sequences and the repeating sequences comprising the plurality of stimulation sequences and the at least one expression sequence, with periods of pauses between certain sequences.

2. The breastpump system of claim 1, wherein providing a plurality of stimulation sequences comprises providing a first stimulation sequence and a second stimulation sequence, wherein the first stimulation sequence comprises a faster cycle rate than the second stimulation sequence.

3. The breastpump system of claim 1, wherein the breastpump session begins with an initiation of one or the plurality of stimulation sequences and the at least one expression sequence and ends with a cessation of all sequences.

4. The breastpump system of claim 1, further comprising:
    a breastpump apparatus; and
    at least one breastshield and container assembly.

5. The breastpump system of claim 1, further comprising:
    a second program following the first program, the second program stored on the memory storage which, when executed by the at least one processor causes the at least one processor to carry out operations comprising:
        providing at least one stimulation sequence and at least one expression sequence in a preset pattern that emulates an irregular suckling pattern of an infant at or after the onset of lactogenesis II, wherein the preset pattern of the first program is different from the preset pattern of the second program.

6. The breastpump system of claim 5, further comprising an input to activate one or both of the first and second programs.

7. The breastpump system of claim 1, wherein each pause of the periods of pauses is an extended pause greater than about three seconds in duration.

8. The breastpump system of claim 7, wherein the extended pause comprises a pause greater than about five seconds in duration.

* * * * *